US009169505B2

(12) United States Patent
Bolz et al.

(10) Patent No.: US 9,169,505 B2
(45) Date of Patent: Oct. 27, 2015

(54) HIGH SOLIDS ENZYME REACTOR MIXER WITH VERTICAL PADDLE AND METHOD

(71) Applicant: Andritz Inc., Glens Falls, NY (US)

(72) Inventors: Edwin William Bolz, Queensbury, NY (US); Rodolfo Romero, Gansevoort, NY (US)

(73) Assignee: Andritz, Inc., Glens Falls, NY (US)

( * ) Notice: Subject to any disclaimer, the term of this patent is extended or adjusted under 35 U.S.C. 154(b) by 84 days.

(21) Appl. No.: 14/063,156

(22) Filed: Oct. 25, 2013

(65) Prior Publication Data

US 2014/0127756 A1 May 8, 2014

Related U.S. Application Data

(60) Provisional application No. 61/723,538, filed on Nov. 7, 2012.

(51) Int. Cl.
| | |
|---|---|
| *C12M 1/00* | (2006.01) |
| *C12M 3/00* | (2006.01) |
| *C12P 19/14* | (2006.01) |
| *B01F 7/16* | (2006.01) |
| *B01F 7/18* | (2006.01) |
| *C12P 19/02* | (2006.01) |
| *C12M 1/40* | (2006.01) |
| *C12M 1/06* | (2006.01) |

(52) U.S. Cl.
CPC ............... *C12P 19/14* (2013.01); *B01F 7/1675* (2013.01); *B01F 7/18* (2013.01); *C12M 21/18* (2013.01); *C12M 23/40* (2013.01); *C12M 27/02* (2013.01); *C12M 27/20* (2013.01); *C12M 39/00* (2013.01); *C12M 45/09* (2013.01); *C12P 19/02* (2013.01)

(58) Field of Classification Search
CPC ...... C12M 27/00; C12M 27/02; C12M 27/08; C12M 23/06
See application file for complete search history.

(56) References Cited

U.S. PATENT DOCUMENTS

| | | | | |
|---|---|---|---|---|
| 4,148,590 | A * | 4/1979 | Sotirianos | 366/288 |
| 2007/0264704 | A1 * | 11/2007 | Van Toever | 435/262 |
| 2009/0285667 | A1 * | 11/2009 | Otto | 415/4.3 |
| 2010/0005711 | A1 * | 1/2010 | McNeff | 47/1.4 |
| 2010/0034050 | A1 * | 2/2010 | Erb et al. | 366/342 |
| 2012/0125549 | A1 | 5/2012 | Romero et al. | |
| 2014/0234896 | A1 * | 8/2014 | McHugh | 435/41 |

FOREIGN PATENT DOCUMENTS

| | | |
|---|---|---|
| FR | 2 325 422 | 4/1977 |
| JP | 2011-120535 | 6/2011 |
| KR | 10-2005-0013269 | 2/2005 |

(Continued)

OTHER PUBLICATIONS

English translation of JP 2011-120535 to Tanaka Hiroshi.*

(Continued)

*Primary Examiner* — Nathan Bowers
(74) *Attorney, Agent, or Firm* — Kerri Hochgesang; Robert Joseph Hornung

(57) ABSTRACT

A reactor vessel including: a mixing chamber having a vertical length, an upper inlet, and a lower outlet; and a vertically oriented paddle within the mixing chamber and having a cross-sectional shape of a hydrofoil, wherein the paddle moves with respect to the mixing chamber.

22 Claims, 7 Drawing Sheets

(56) References Cited

FOREIGN PATENT DOCUMENTS

| | | |
|---|---|---|
| WO | 2012/125730 | 9/2012 |
| WO | 2012/130777 | 10/2012 |

OTHER PUBLICATIONS

International Search Report cited in PCT/US2013/068897 mailed Jan. 23, 2014.

* cited by examiner

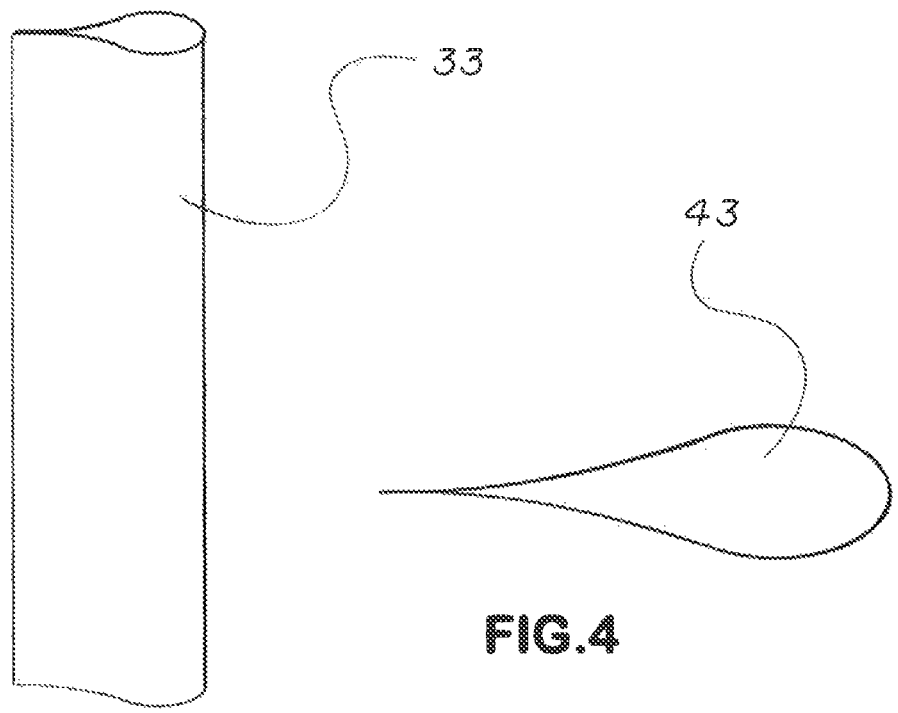
FIG.3
FIG.4
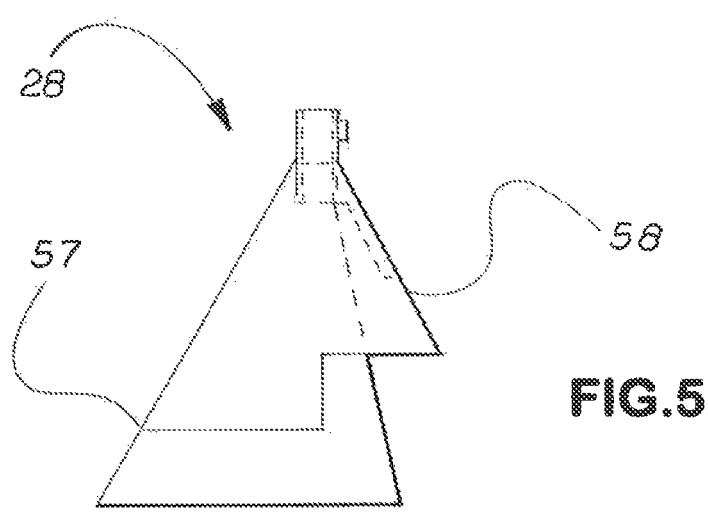
FIG.5

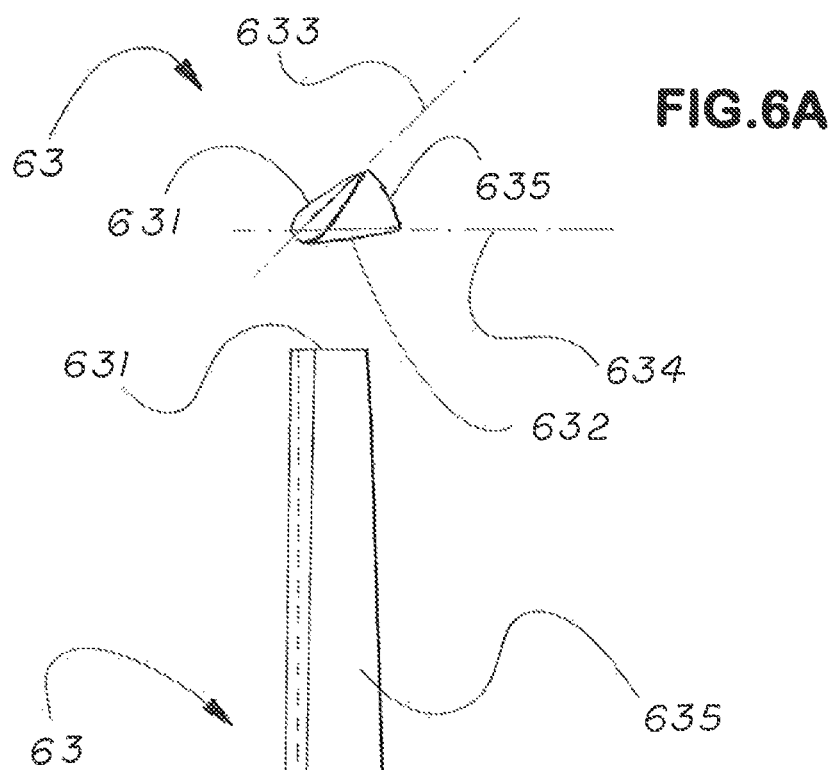
FIG. 6A
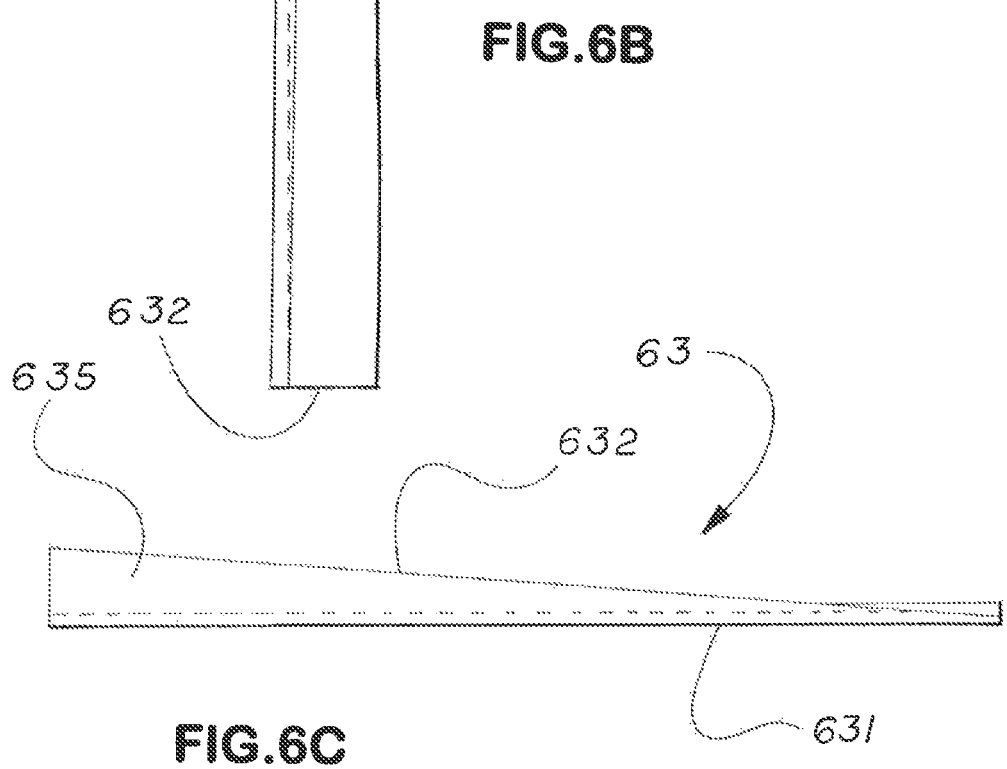
FIG. 6B
FIG. 6C

HIGH SOLIDS ENZYME REACTOR MIXER WITH VERTICAL PADDLE AND METHOD

RELATED APPLICATION

This application claims priority to and incorporates by reference provisional Application 61/723,538 filed Nov. 7, 2012.

TECHNICAL FIELD

Example embodiments of the invention relate generally to the field of enzymatic conversion of biomass to monomeric sugars and particularly to mixing the biomass with enzymes to promote hydrolysis.

BACKGROUND OF THE INVENTION

Biomass feedstock may be solely lignocellulosic material or a mixture of lignocellulosic and other materials. Polysaccharide biomass is typically a mixture of starch and lignocellulosic materials. The starch may be contained in grains or a refined starch added as feedstock to form the biomass. The biomass feedstock may also include polymers and other materials.

Enzymes are mixed with the biomass to promote hydrolysis. Mixing ensures the enzymes continually and repeatedly move into contact with chemical reaction sites in the biomass to promote hydrolysis or other degradation of the biomass. In addition, or in place of enzymes, other cellulose degrading organisms and biocatalysts may be added to the biomass to promote hydrolysis or other degradation of the biomass.

The feedstock of lignocellulosic material and enzymes or other degrading materials are mixed together to form the biomass mixture. This biomass mixture may have characteristics similar to a high matter content powder. Liquid may also be added to the biomass mixture to form a high viscosity liquid slurry. Liquid may be added to liquefy the biomass solids and generate a uniform biomass emulsion formed of feedstock and liquids, which have significant differences in their characteristics.

Mixers, constant-stir reactors, and other similar mixing or agitation devices may be used to mix and liquefy the feedstock and enzymes to form the biomass mixture. These devices conventionally are cylindrical vessels arranged vertically and have mechanical mixing devices, such as stirrers having radial arms and blades. These mixing devices generally rotate about a vertical shaft and move through the biomass, with mixing occurring for a period of time depending of the feedstock used.

Enzymatic liquefaction of lignocellulosic feedstock to biomass may require several hours of mixing. A result of the mixing is the reduction of the viscosity of the biomass. The enzymes convert the generally solid biomass composition into liquefied slurry. Biomass pretreated for enzymatic conversion to monomeric sugars typically starts the mixing process having a fibrous or mud-like consistency. The enzymes added to the biomass typically have a relatively low concentration with respect to the biomass. The biomass and enzyme mixture tends to be highly viscous as it enters the mixer and pretreatment hydrolysis reactor system. There could be one or more hydrolysis reactor vessels in the system.

Because of the high viscosity of the biomass entering the hydrolysis reactor vessel, a large force (torque) is needed to turn the mixing devices and properly mix the enzymes with the biomass. The mixing force traditionally limits the size of the mixing vessels. Many of the conventional vessels where mixing occurs tend to be small diameter vessels as the torque needed to rotate the mixing arms increases exponentially with the radial length of the arms. Due to the high viscosity of the biomass, the radial length of the arms is traditionally short so they can move through the biomass. Motors used to turn the mixing arms have a maximum power limitation, contributing to the constraint of the maximum length of the mixing arms. As a result of the constraints of the motor and mechanical strength of the mixing components, the vessels used for mixing the high viscosity pretreated biomass have conventionally been small and narrow.

For these reasons, and others, the mixing vessels for enzymatic liquefaction of lignocellulosic biomass have conventionally been operated in batch rather than continuous mode and frequently require the simultaneous operation of multiple batch mixing vessels to feed a larger downstream vessel.

A large continuous mode mixing vessel capable of mixing the highly viscous biomass and enzymes has recently been developed as described in US Patent Application Publication 2012-125549 (the "'549 Application"). In this system the enzymatic hydrolysis and mixing process relies on physical forces, such as gravity and centrifugal force, to ensure the biomasses are subjected to the desired mechanical forces.

In the continuous mixing and reactor device, a first internal mixing chamber has a cross-sectional area expanding from the biomass inlet to the internal area of a second chamber with a uniform internal cross-sectional area throughout the second chamber. In this system, the biomass reactor contains the rotating mixing device and is coaxial with the reactor vessel. This mixing chamber can be comprised of multiple zones at different elevations in the vessel. The mixing is caused by horizontal paddles or trays and also allows for the movement of the material vertically down the vessel. The liquefied slurry flows from the lower zones of the mixing vessel, with a portion of the slurry pumped or circulated to the upper zones of the vessel to adjust the slowly changing viscosity of the feedstock at the upper elevations of the vessel.

While the use of the system and method described in the '549 Application has allowed for continuous operation of a mixing and reactor vessel, the vertical mixing which results from the method of the '549 Application has been found to reduce the desirable plug flow needed for good control of viscosity reduction as the material moves through the reactor vessel. A "plug flow" refers to a flow with a substantially constant velocity across a given area. The desired plug flow promotes consistent retention time in the reactor vessel and avoids regions in the vessel of stagnant biomass.

SUMMARY OF THE INVENTION

The biomass and enzyme material tends to rotate at a slower rate than the paddles because of the drag of the biomass and enzyme material. As the biomass and enzyme material slowly descends down the mixing chamber of the reactor vessel, the enzymes react with the biomass and the viscosity of the biomass and enzyme material changes. Unfortunately, as the viscosity of the biomass and enzyme material changes, so do the drag and the rotation speed of the biomass and enzyme material, which causes rotation deltas throughout the length of the mixing chamber. The inventors have recognized that vertical paddles having a varying hydrofoil cross-section or angle of attack may be used to keep the rotation of the biomass and enzyme material substantially constant over the entire length of the mixing chamber. This design may promote plug flow and reduce rotation deltas.

To promote plug flow, improve mixing, and reduce stagnant regions in the mixing chamber of the reactor vessel, a new vertically-oriented paddle with a hydrofoil shape has been conceived for mixing biomass and enzyme material. In example embodiments, the "angle of attack" (i.e. the angle at which the paddle engages the biomass and enzyme material) may vary along the length of the paddle. In other embodiments, the cross-sectional area of the paddle along a horizontal plane may vary along the length of the paddle.

It is desirable to have a slow and uniform plug flow of material vertically down the mixing chamber of the reactor vessel. A slow, constant plug flow movement may be desirable to ensure a less aggressive mixing than in the prior art vessels where mixing occurred resulting in material from a lower elevation in the mixing chamber being pushed up the mixing chamber, thus disrupting plug flow. Rather than moving biomass and enzyme material up in the mixing chamber of a reactor vessel, a horizontal blending of the biomass and enzyme material at all vertical positions within the mixing chamber may reduce areas of stagnant material.

Within the mixing chamber of the reactor vessel, the movement of the biomass and enzyme material is desirably uniform and slow to avoid stagnant regions of biomass and enzyme material and to allow sufficient time for the reactions to occur to the biomass. The horizontal blending motion of the biomass and enzyme material within the mixing chamber may help to establish and maintain the desired reaction environment. A desirable reaction environment may include optimal temperature ranges for the enzymes. Slow horizontal blending can create plug flow, and plug flow is generally desirable for a more controllable reaction pattern.

To provide the desired horizontal blending movement or motion, one or more vertical paddles with a hydrofoil shape may be used in the mixing chamber of the reactor vessel. More than one vertical paddle may be arranged in an array around a center shaft. The length of the vertical paddles can be substantially, as in 80% or more, the vertical length of the mixing chamber of the reactor vessel. If desired, the length of the paddles may be a reduced length, such as at least 75% the height of the body of the vessel.

The vertical paddles may be attached at each end to a top support bar and a bottom support bar. Each support bar in turn may be horizontally attached to a center shaft running the vertical length of the mixing chamber. The center shaft is attached to a motor capable of moving the support bars and therefore the paddles, vertically, in unison, in a single direction, in a slow circular motion about the center shaft of the mixing chamber. The hydrofoil design may allow for the paddles to have an offset from vertical angle in a range of negative 25 degrees to positive 25 degrees depending on the viscosity of the biomass and enzyme material. In other example embodiments, a range of positive 15 degrees to negative 15 degrees may be desirable for mixing biomaterial and enzymes where the biomaterial may be derived from wood pulp, bagasse, or agricultural residue. In certain embodiments, the offset from the vertical angle may vary along the vertical length of the paddle. For example, the paddle may have a vertical offset angle of 2 degrees at the first end of the vertical paddle and a vertical offset angle of 15 degrees at a second end of the vertical paddle. This offset from vertical may provide a smooth, uniform movement of the biomass and enzyme material within the mixing chamber of the reactor vessel at many vertical points in the mixing chamber.

A reactor vessel has been conceived comprising: a mixing chamber having a vertical length, an upper inlet, and a lower outlet; and at least one paddle having a vertical orientation within the mixing chamber and the at least one paddle having a cross-sectional shape of a hydrofoil, wherein the at least one paddle moves with respect to the mixing chamber while maintaining the vertical orientation.

In other embodiments, the vertical paddles may be attached at each end to a top support bar and a bottom support bar. Each support bar in turn may be attached to a center shaft that does not extend into the mixing chamber beyond the top and bottom support bars that engage the vertical paddles. One or both ends of the shaft may be attached to a motor capable of moving the support bars and therefore the paddles, vertically, in unison, in a single direction, in a slow circular motion about the center vertical axis of the mixing chamber.

In other embodiments, the cross-sectional area of the vertical paddle, as measured along a horizontal plane, may vary along the length of the vertical paddle. For example, the width of the vertical paddle may be thicker at one end of the vertical paddle than the width would be at another end of the vertical paddle. This variation in cross-sectional area may also provide a smooth, uniform movement of the biomass and enzyme material within the mixing chamber at many vertical points in the mixing chamber.

In still other embodiments, a reactor vessel has been conceived comprising: an internal cylindrical mixing chamber, a center shaft extending the length of the internal cylindrical mixing chamber, a motor drivingly coupled to the center shaft, an upper support bar within the internal cylindrical mixing chamber and extending outward from an upper section of the center shaft, a lower support bar within the internal cylindrical mixing chamber and extending outward from a lower section of the center shaft; and at least one vertical paddle supported by and attached to the upper support bar and the lower support bar, wherein the at least one vertical paddle moves around the center shaft.

This movement of the biomass and enzyme material in the mixing chamber in a generally vertical, uniform, continuous and slow flow may ensure a desired plug flow of the biomass enzyme material from the mixing chamber inlet to the mixing chamber outlet. Biomass and enzyme material in the mixing chamber may be at a temperature of between 20° C. and 60° C., such as, 40° C. to 50° C. for thermophillic enzymes such as cellulases. A range of 25° C. to 30° C. may be desirable for mesophillic enzymes, and a range of 20° C. to 25° C. may be desirable for enzymes used in simultaneous saccharification and fermentation ("SSF"). The SSF process involves mixing enzymes such as cellulase enzymes with yeast. The time the biomass and enzyme material spend within the mixing chamber may be between 1 to 5 hours. The range may vary depending on the type of enzyme used. A range of about 2.5 to 3.5 hours may be desirable for cellulase enzymes, and a range of about 3 hours may be desirable for cellulase enzymes reacting with biomaterial such as wood chip, bagasse, and agricultural residue. The biomass and enzyme material retention period in the mixing chamber should be sufficient to affect the viscosity of the biomass and enzyme material from an entering viscosity of over 15,000 centipoise "cP" at the top of the mixing chamber to a biomass and enzyme material having a viscosity of less than 1,000 cP at a lower discharge end of the mixing chamber.

When using the vertical paddle design it may not be necessary to use any horizontal mixing arms above or below the vertical paddles.

To further improve the use of the vertical paddles within the mixing chamber, a "flow cone" may be attached to the center shaft, such as near the top support bar holding the paddles or baffles. The flow cone may be hollow. Additionally, the flow cone may have cut-out sections along the sides, such that the sides of the flow cone may not be uniform in length from the top to the bottom of the flow cone. The cut-out sections provide at least a part of the side of the flow cone to be open while another section of the side of the flow cone may be extend to the bottom of the flow cone. Due to the cut-out sections of the flow cone, the support bar to which the paddles or paddles are attached at the top end of the paddles can be at least partially covered by the flow cone at one end, while the opposite end of the support bar may be uncovered.

A system is disclosed, wherein a slurry material of biomass is fed to a reactor vessel comprising: at least one vertically orientated hydrofoil-shaped baffle or paddle connected at each end to a support bar, wherein the support bar is connected to a center shaft positioned at or near the center vertical axis of the mixing chamber, with the center shaft attached to a motor to provide motion to the center shaft thereby moving the baffles in unison, in a unidirectional manner, throughout substantially the entire length of the mixing chamber.

Another embodiment may include the use of a flow cone attached to the center shaft near the top support bar holding the hydrofoil-shaped paddles. The flow cone is a hollow cone with side sections removed to allow for smooth movement of slurry material entering the mixing chamber to be distributed substantially evenly over the circular area of the mixing chamber.

A method is disclosed herein in which a slurry material of Biomass and enzyme material in the mixing chamber may be at a temperature of between 20° C. and 60° C. For example, a range of 40° C. to 50° C. may be desirable for thermophillic enzymes. A range of 25° C. to 30° C. may be desirable for mesophillic enzymes, and a range of 20° C. to 25° C. may be desirable for enzymes used in SSF. The time the biomass and enzyme material spends within the mixing chamber may be between 1 to 5 hours. The range may vary depending on the type of enzyme used. A range of about 2.5 to 3.5 hours may be desirable for cellulase enzymes, and a range of about 3 hours may be desirable for cellulase enzymes reacting with biomaterial such as wood chips, bagasse, and agricultural residue. The temperature, mixing, and length of time the biomaterial and enzymes spend in the mixing chamber allow for a change in the viscosity of the slurry material of biomass and enzymes from its entering viscosity of over 15,000 cP at the top of the reactor vessel to a slurry material of biomass and enzymes having a viscosity of less than 1,000 cP; mixing the slurry material of biomass and enzymes using a vertically orientated hydrofoil-shaped baffle or paddle in a unidirectional manner, substantially the entire length of the mixing chamber; discharging the lower viscosity slurry material of biomass and enzymes from the mixing chamber.

In another embodiment, the vertically oriented hydrofoil-shaped paddles or paddles may rotate at different rates. In still other embodiments, the vertically oriented hydrofoil-shaped paddles or paddles may rotate in opposing directions. In other embodiments, the vertically orient hydrofoil-shaped paddles or paddles may move non-uniformly through the mixing chamber. In another embodiment, concentric paddles or paddles may rotate in opposite directions such that one set of paddles, comprising at least one paddle may move around a center axis in a clockwise direction while another set of paddles, comprising at least one paddle may move around the center axis in a counter-clockwise direction. The angles of attack of the hydrofoil-shaped paddles or paddles may be adjusted to reduce incidences of vertical agitation of the enzyme and biomass material. Adjusting the angle of attack of the hydrofoil-shaped paddles or paddles may thereby promote plug flow.

In yet another embodiment, paddles may occupy quadrants of the mixing chamber, such that the paddles extend to one half the length of the mixing chamber from the top and bottom of the mixing chamber. Paddles occupying one quadrant may move in a different direction from paddles occupying other quadrants. Additionally, at least one paddle within a quadrant may move in at least one direction, while at least a second paddle in the quadrant moves in a second direction.

Another method of mixing biomass and an enzyme in a reactor vessel using a vertically-oriented mixing chamber and at least one paddle blade extending vertically through the mixing chamber is disclosed: feeding a mixture of biomass and enzyme continuously into an upper inlet of the reactor vessel and adding the mixture of biomass and enzyme into the mixing chamber; moving the at least one paddle blade through the mixture of biomass and enzyme in the mixing chamber while maintaining the at least one paddle blade in a vertical orientation; mixing the mixture of biomass and enzyme by the movement of the at least one paddle blade as the mixture of biomass and enzyme moves down through the mixing chamber; and discharging the mixture of biomass and enzyme from a lower outlet of the reactor vessel.

Another method is disclosed herein in which a slurry material of biomass and enzymes is fed to a reactor vessel comprising: as the slurry of biomass and enzyme material at a temperature of between about 20° C. and 60° C. For example, a range of 40° C. to 50° C. may be desirable for thermophillic enzymes. A range of 25° C. to 30° C. may be desirable for mesophillic enzymes, and a range of 20° C. to 25° C. may be desirable for enzymes used in SSF. The time the biomass and enzyme material spends within the mixing chamber may be between 1 to 5 hours. The range may vary depending on the type of enzyme used. A range of about 2.5 to 3.5 hours may be desirable for cellulase enzymes, and a range of about 3 hours may be desirable for cellulase enzymes reacting with biomaterial such as wood chips, bagasse, and agricultural residue. The temperature, mixing, and length of time the biomaterial and enzymes spend in the mixing chamber allow for a change in the viscosity of the slurry of biomass and enzyme material from its entering viscosity of over 15,000 cP at the top of the reactor vessel to a slurry of biomass and enzyme material having a viscosity of less than 1,000 cP at the bottom of the reactor vessel. The slurry of biomass and enzyme material is contacted with a flow cone attached to the center shaft near the top support bar holding the hydrofoil-shaped paddles providing for smooth movement of the slurry of biomass and enzyme material entering the mixing chamber of the reactor vessel to be distributed substantially evenly over the circular area of the mixing chamber. The slurry of biomass and enzyme material is mixed using a vertically orientated hydrofoil-shaped baffle or paddle in a unidirectional manner, substantially the entire length of the mixing chamber. The lower viscosity material is discharged from the mixing chamber.

In another embodiment, a reactor vessel has been conceived comprising: a cylindrical mixing chamber having a vertical axis; at least one vertical paddle supported by an upper support bar and a lower support bar; a center shaft extending along the vertical axis of the cylindrical mixing chamber, wherein the upper and lower support bars are attached to and extend radially outward from the center shaft; an engine or motor external to the reactor vessel and drivingly coupled to the center shaft to rotate the center shaft, an upper support bar and a lower support bar and the at least one vertical paddle; a conical deflector having a peak aligned with the vertical axis and positioned above the at least one vertical paddle.

Corresponding reference characters indicate corresponding parts throughout the several views. Although the drawings represent embodiments of various features and components according to the present disclosure, the drawings are not necessarily to scale and certain features may be exaggerated in order to better illustrate embodiments of the present disclosure, and such exemplifications are not to be construed as limiting the scope of the present disclosure in any manner.

BRIEF DESCRIPTION OF THE DRAWINGS

FIG. 3 shows a side view of an example embodiment of a vertical paddle.

FIG. 4 is a top view of an example embodiment of the hydrofoil shape of the vertical paddle.

FIG. 5 shows a side view of an exemplary flow cone.

FIG. 6A shows a top down view of an exemplary vertical paddle with a hydrofoil shape and a non-uniform vertical axis offset angle.

FIG. 6B shows a side view of the front of the vertical paddle shown in FIG. 6A.

FIG. 6C shows a top down view of an exemplary vertical paddle with a planar shape and a non-uniform vertical axis offset angle.

DETAILED DESCRIPTION OF THE INVENTION

Figures 1, 2:
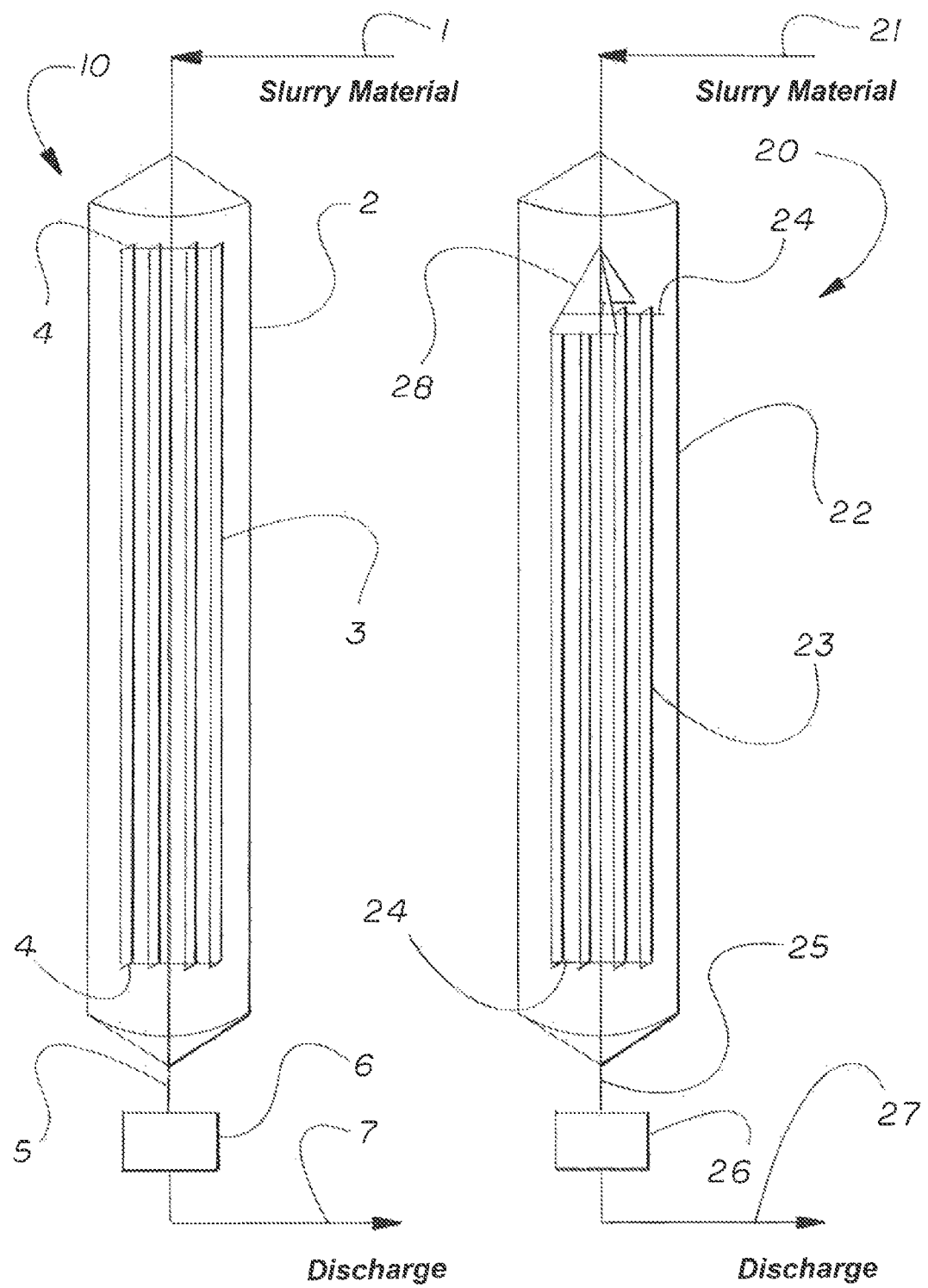
FIG. 1 shows a side view of an example embodiment of a vertical cylindrical reactor vessel with vertical paddles.
FIG. 2 shows a side view of an example embodiment of a vertical cylindrical reactor vessel with vertical paddles and a flow cone.

The flow cone may be attached to the center shaft and may be positioned to allow the support bar at the top end of the paddles to fit at the bottom of the flow cone or just inside the flow cone. Because the flow cone is attached to the center shaft, it moves in the same motion of the center shaft. As slurry material of biomass and enzymes enters the mixing chamber, the slurry material of biomass and enzymes contacts the flow cone and moves along outer surface of the flow cone. The flow cone may direct the flow of the slurry material of biomass and enzymes entering the vessel to all parts of the body of the mixing chamber. The flow cone may also distribute the flow of slurry material and biomass along the circular area of the mixing chamber without preference to any one area of the mixing chamber. As a result, the flow cone may form a thick padding-like layer along the surface of the mixing chamber to avoid liquid less fully incorporated in the slurry from gathering along the inner core of the mixing chamber. The cut-out sections of the flow cone allow some slurry material of biomass and enzyme to fall into the area of the paddles, while other slurry material of biomass and enzymes may be directed toward the mixing chamber walls. The shorter sections of the flow cone provide an opening to the paddle region, while the longer sections of the flow cone move the slurry material of biomass and enzymes toward the mixing chamber walls.

The use of the flow cone may promote an even distribution of the slurry material of biomass and enzymes across a circular cross-section of the mixing chamber. The flow cone may thereby enhance the ability of the enzymes within the slurry material of biomass and enzymes to react and promote the desired viscosity change in a plug flow fashion. In this manner, the flow cone may promote the desired plug flow and liquefaction of the biomass.

Features of the reactor vessel disclosed herein comprise: paddles vertically oriented in a mixing chamber of the vessel, the paddles supported by and attached to support bars at the upper and lower ends of the paddle and attached to a rotating center shaft of the mixing chamber. The paddles may have a cross-sectional shape of a hydrofoil and may have a non-uniform cross-sectional shape along their length to minimize the tendency of the paddles to cause biomass and enzyme material to change elevation in the mixing chamber. The hydrofoil cross-section is a shape designed to move through the biomass and enzyme material and include cross-sectional shapes such as for airfoils, wings or fins, and may have cross-sections shaped as a teardrop, diamond, crescent or ellipse. The paddles may rotate in a slow, constant, unidirectional manner, e.g., less than 10 revolutions per minute, to prompt mixing of biomass and enzyme material at the same elevation. The paddle's slow, constant, unidirectional movement reduces of the tendency of the mixing action to change the elevation of the biomass and enzyme material. This movement may also allow the biomass and enzyme material to move downward in a uniform, slow, and continuous manner while the biomass and enzyme material is being mixed.

In some embodiments, the reactor vessel may further comprise a scrapper baffle supported by a scrapper support bar extending radially from the center shaft wherein the scrapper baffle engages an inner wall of the mixing chamber.

A deflector, such as a conical deflector or flow cone, at the upper region of the mixing chamber and immediately below the biomass and enzyme input to the mixing chamber may distribute the biomass and enzyme material evenly in the upper region of the mixing chamber. The deflector may be mounted to the upper support bars extending radially from the center shaft to the upper end of the paddles. The deflector may have a peak coaxial with the center shaft, aligned vertically with the biomass and enzyme input to the reactor vessel or both. The deflector may have an irregular perimeter and cut-outs to promote even distribution of the biomass and enzyme material in the mixing chamber. The deflector may be a flow cone that has a conical surface, is hollow, has cut-outs in the conical surface, and has a lower perimeter with sections at different radii from the center axis and staggered in step.

The flow cone assists in evenly distributing the biomass and enzyme slurry material across the interior of the mixing chamber. The even distribution of the biomass and enzyme material promotes even distribution of the enzymes in the biomass and uniform reactions between the enzymes and the biomass. The flow cone avoids the buildup of material toward the center of the mixing chamber, which otherwise would create a column of more viscous biomass and enzyme material in the center of the mixing chamber. This more viscous biomass and enzyme material would push upward a less viscous biomass and enzyme material located at the bottom of the mixing chamber.

The deflector may cause a portion of the biomass and enzyme material to form a thick annular pad adjacent to the wall of the mixing chamber. The pad prevents liquid less fully incorporated into the slurry of biomass and enzyme material from gathering along the wall of the mixing chamber and flowing in channels down through the mixing chamber, thereby creating problematic rotation deltas.

FIG. 1 shows a reactor vessel 10 for mixing and retaining a highly viscous feed slurry material of biomass and enzymes 1. The slurry material of biomass and enzymes 1 may enter the mixing chamber 2 at a viscosity of over 15,000 cP and react with the enzymes in the mixing chamber 2. In some embodiments, the mixing chamber 2 may have a vertical length of at least one hundred feet and a diameter of at least 30 feet. The reacted biomass slurry 7 may have a relatively low viscosity of about 1,000 cP at the discharge of the mixing chamber.

The mixing chamber 2 may be equipped with at least one paddle 3 attached at either end of the paddle to support bar 4. The paddle 3 may be vertically-oriented and may be coated to prevent adhesion of the biomass and enzyme material. This coating may be a polytetraflouroethylene material such as DuPont brand TEFLON or other suitable coating material. Such suitable materials may include materials that provide a non-stick surface. In some embodiments, it may be desirable for the coating material to withstand caustic environments. In other embodiments, it may be possible to have a coating material capable of withstanding a basic environment or a neutral pH environment. The mixing chamber 2 may also and may be coated to prevent adhesion of the biomass and enzyme material. This coating may be a polytetraflouroethylene material such as DuPont brand TEFLON or other suitable coating material. The mixing chamber 2 may also be internal to the reactor vessel 10. By being attached to the support bar 4 at each end, the paddle 3 remains rigid. The support bar 4 is attached to the center shaft 5 positioned substantially along the center axis of the mixing chamber 2. Center shaft 5 may be attached a motor 6. Center shaft 5, via motor 6, moves in a circular motion to allow all of the paddles 3 to move simultaneously in a slow, constant, unidirectional manner within the mixing chamber 2.

As the slurry material of biomass and enzymes 1 moves down through the mixing chamber 2, the enzymes react with the biomass in the slurry material of biomass and enzymes 1 to reduce the viscosity of the biomass and enzyme material from about 15,000 cP to about 1,000 cP, at the bottom of mixing chamber 2. The reacted biomass slurry 7 may be sent out of the mixing chamber 2 for further processing.

Paddle 3 can be attached to the support bar 4 so that the angle of the paddle 3 relative to the vertical axis of the paddle 3 is in a range of negative 25 degrees to positive 25 degrees depending on the viscosity of the biomass and enzyme material. In other example embodiments, a range of positive 15 degrees to negative 15 degrees may be desirable for mixing biomaterial and enzymes where the biomaterial is derived from wood pulp, bagasse, or agricultural residue.

If desired, the angle offset from the vertical axis of paddle 3 may vary along the vertical length of the paddle 3. This embodiment is described in more detail in FIGS. 6A, 6B and 6C.

In other embodiments, the cross-sectional area of the paddle 3, as measured along a horizontal plane, may vary along the length of the vertical paddle 3 such that the width of the paddle 3 may be greater at one location along the paddle than at another location along the paddle 3. This embodiment is described in more detail in FIGS. 6A, 6B and 6C.

FIG. 2 shows a vertical cylindrical reactor vessel 20, with the addition of a flow cone 28. The flow cone 28 may be attached to the center shaft 25 at the top of the mixing chamber 22 just above the support bar 24. The support bar 24 at the top of the mixing chamber 22 may engage the vertical paddles 23. A motor 26 may also engage and rotate the center shaft 25. The flow cone 28 is shown in more detail in FIG. 5.

FIG. 3 shows a section of a paddle 33 used in the reactor vessels of FIGS. 1, 2, 7A and 7B. The paddle 33 may be substantially between 90% or 80% the length of the mixing chamber 2 of FIG. 1, or it can be less than the entire length, such as greater than 50% the length of the mixing chamber 2. A length of the paddles greater than 50% of the mixing chamber 2 may be desirable to promote plug flow of biomaterial such as wood chips, bagasse, and agricultural residue.

FIG. 4 shows an exemplary design for the paddle. The paddle has a hydrofoil design 43 which allows for a smooth movement of the biomass and enzyme material 1 as it moves helically in a plug flow fashion down the length of the mixing chamber 2 of FIG. 1.

FIG. 5 shows the cut-away areas of the flow cone 28. Sides of the cone are of different lengths, for example one side 58, may be shorter than the opposite side 57. The flow cone 28 may be hollow, and may fit over the support bar 24 of FIG. 2. The flow cone 28 may be coated to prevent adhesion of the biomass and enzyme material. This coating may be a polytetraflouroethylene material such as DuPont brand TEFLON or other coating suitable material. The flow cone 28 distributes the slurry material of biomass and enzymes 21 entering the reactor vessel 20 uniformly over a circular area of the reactor vessel 20 and may form a thick padding-like layer of biomass and enzyme material along the inner surface of the mixing chamber 22. The padding layer prevents liquid not fully incorporated in the slurry of biomass and enzyme material from gathering and forming an inner core of heavier, more viscous material. Such a core may travel down the mixing chamber 22 and push upward less viscous material located at the bottom of the mixing chamber 22 thus disrupting plug flow.

FIG. 6A shows a top view of an exemplary paddle 63. The paddle 63 has a hydrofoil shape and a non-uniform offset angle from the vertical axis known as the angle of attack. The top 631 of the paddle 63 may define a first ray 633. The bottom 632 of the paddle 63 may define a second ray 634. The body 635 of the paddle 63 spans the angle created by first ray and second ray to create a non-uniform angle of attack along the length of the paddle 63.

FIG. 6B shows a side view of paddle 63 whereby the body 635 of the paddle has a non-uniform angle of attack defined by the top 631 and the bottom 632 of the paddle 63.

FIG. 6C is another top down view of an exemplary paddle 63. The paddle 63 may be planar and the cross-sectional area of the bottom 632 of the paddle 63 may be greater than the cross-sectional area of the top 631 of the paddle 63 to form a body 635 of the paddle 63 with a non-uniform cross-sectional area. This embodiment also shows how the non-uniform cross sectional area can be used to form a non-uniform angle of attack.

Figure 7A:
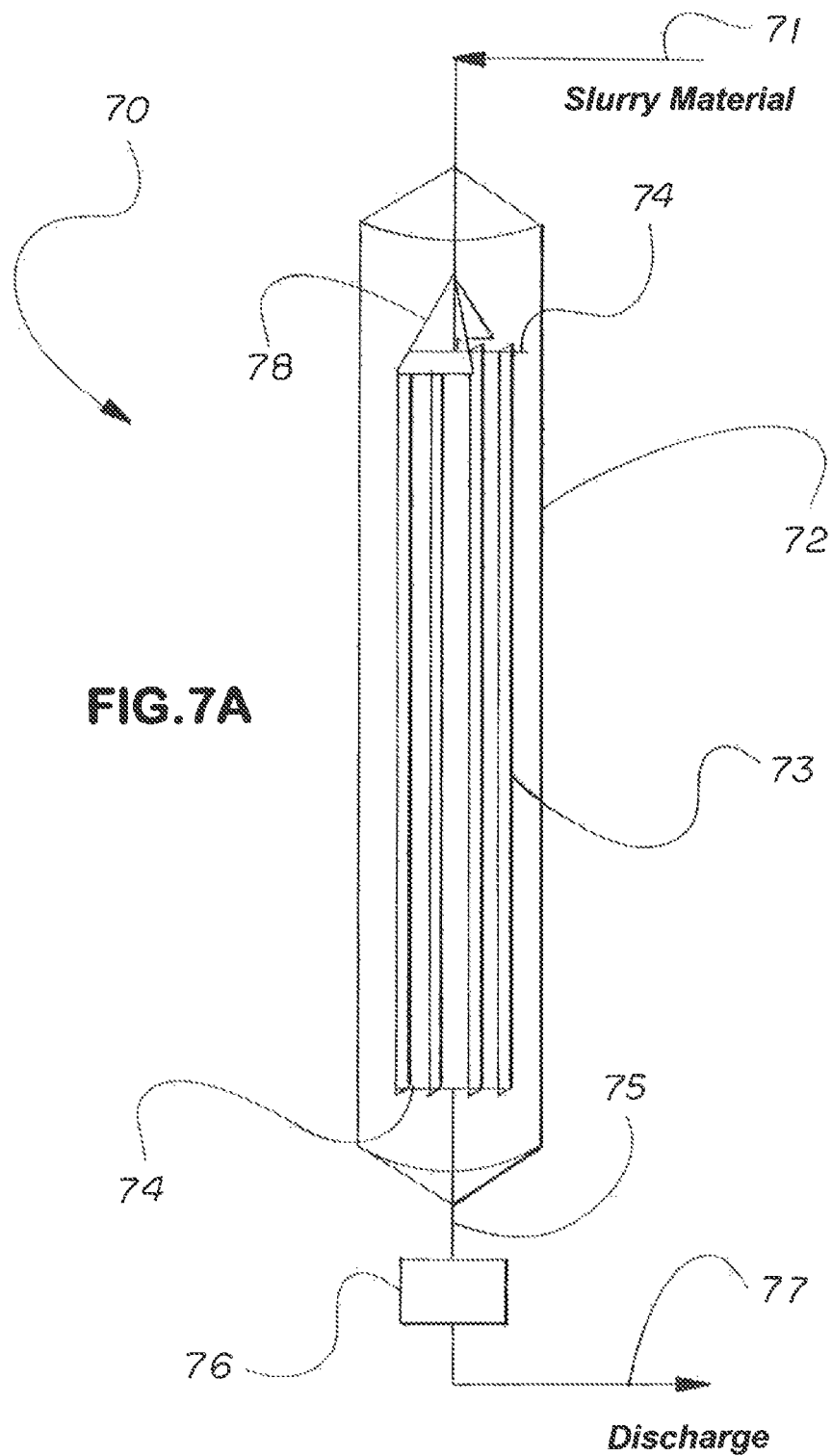
FIG. 7A depicts an example embodiment of the vertical cylindrical reactor vessel with vertical paddles and a flow cone and a center shaft that does not extend significantly into the mixing chamber.

FIG. 7A shows an example embodiment of a vertical cylindrical reactor vessel 70, with the addition of a flow cone 78. The flow cone 78 may be attached to the center shaft 75. The center shaft may not extend past the support bars 74 at the top or bottom of the mixing chamber 72. A motor 76 may engage and rotate the center shaft 75. Reacted biomass slurry 77 may be sent out of the mixing chamber 72 for further processing.

Figure 7B:
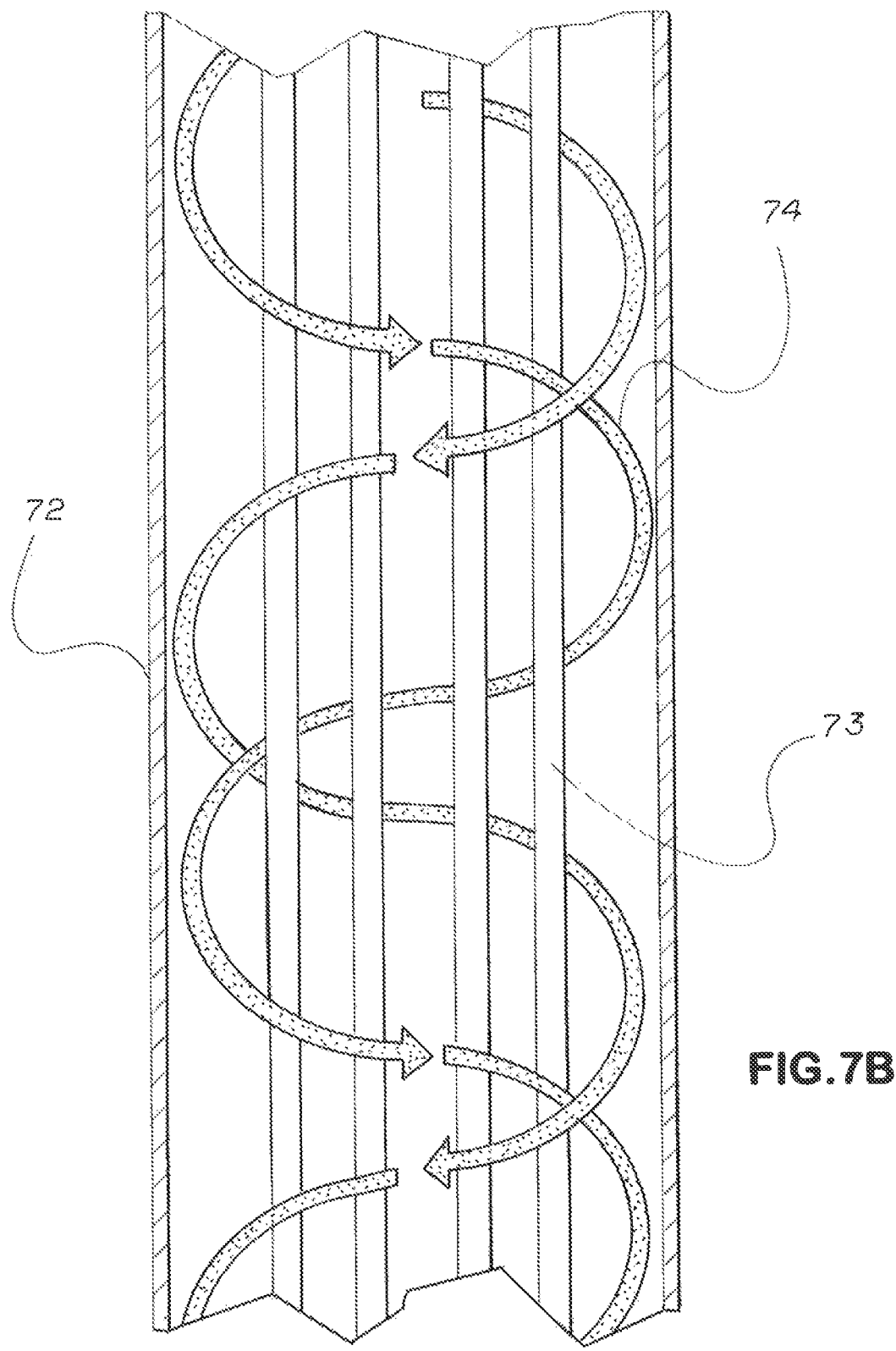
FIG. 7B depicts a helical path optimally taken by a particle in the biomass and enzyme material as it flows down the mixing chamber.

FIG. 7B depicts the ideal plug flow path of a particle within the biomass and enzyme material. In an embodiment where the vertical paddles 73 move in substantially the same direction, a particle within the biomass and enzyme material tends to move downward through the mixing chamber 72 in a helical path 721.

Figure 8A:
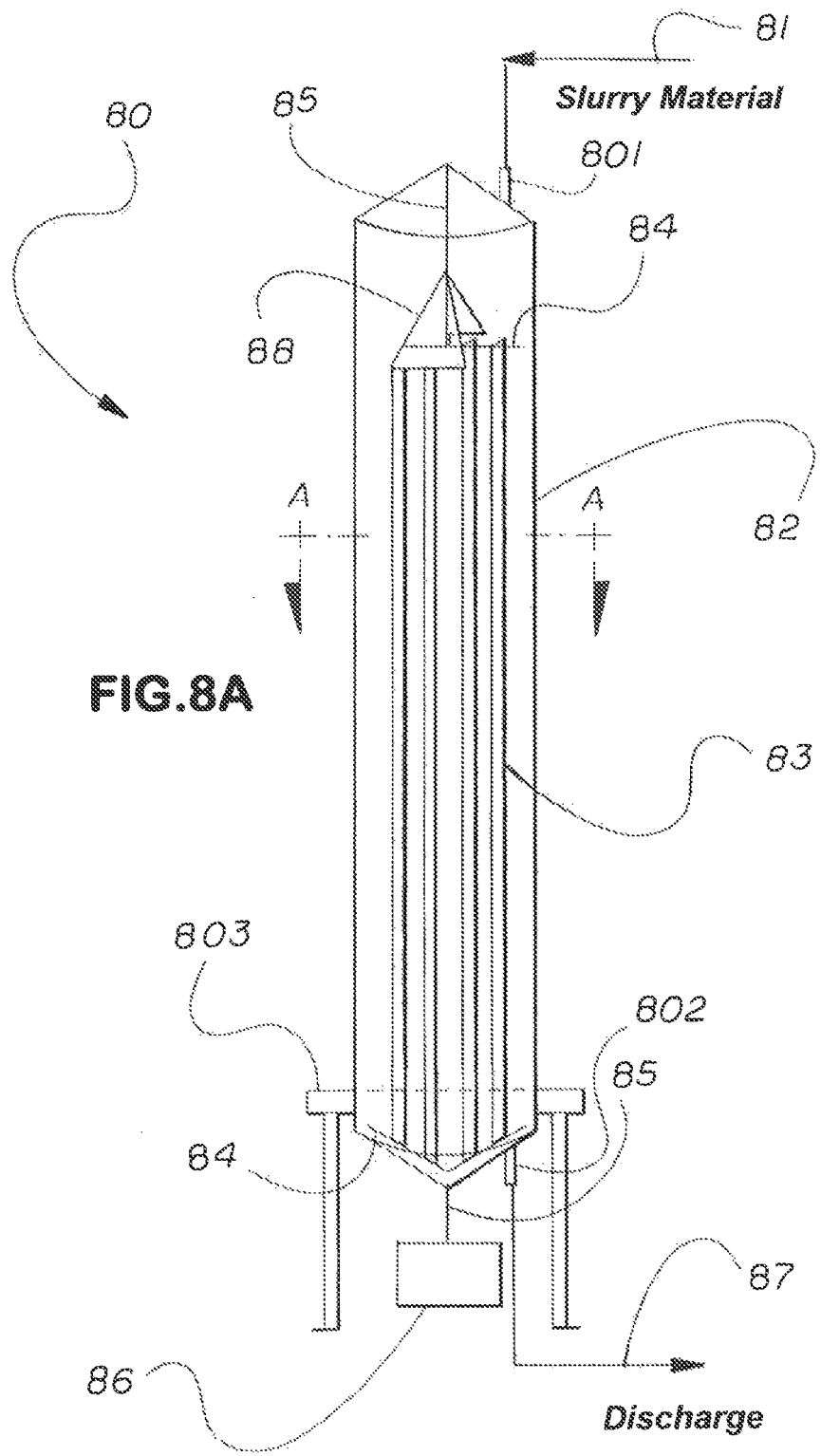
FIG. 8A depicts an example embodiment of the vertical cylindrical reactor vessel with vertical paddles extending substantially the entire height of the cylindrical height of the mixing chamber.

FIG. 8A shows an example embodiment of a vertical cylindrical reactor vessel 80, with the addition of a flow cone 88. The vertical cylindrical reactor vessel 80 may be supported by a vessel support stand 803. The flow cone 88 may be attached to the center shaft 85. A motor 86 may engage and rotate the center shaft 85. The center shaft may not extend past the support bars 84 at the top or bottom of the mixing chamber 82. In this example embodiment, the support bars may bend with or take on the contours of the top and bottom of the mixing chamber 82. The paddles 83 may move in a slow, manner within the mixing chamber 82. This embodiment depicts the paddles 83 spanning substantially the entire length of the mixing chamber 82. In this example embodiment, a scrapper paddle 805 may be used to dislodge biomass and enzyme material from the inner wall of the mixing chamber 820. This is explained more fully in FIGS. 8B and 8C. The motion of the paddles 83 and the scrapper paddle 805 may ensure the desired plug flow of the biomass and enzyme material 81 from the mixing chamber inlet 801 to the mixing chamber outlet 802. The mixing chamber inlet 801 may be substantially centered on the center axis at the top of the mixing chamber 82 or the mixing chamber inlet 801 may be off-centered from the center axis of the mixing chamber 82. Likewise, the mixing chamber outlet 802 may be substantially centered on the center axis of bottom of the mixing chamber 82 or the mixing chamber outlet 802 may be off-centered from the center axis of the mixing chamber 82. Reacted biomass slurry 87 may be sent out of the mixing chamber 82 for further processing.

Figure 8B:
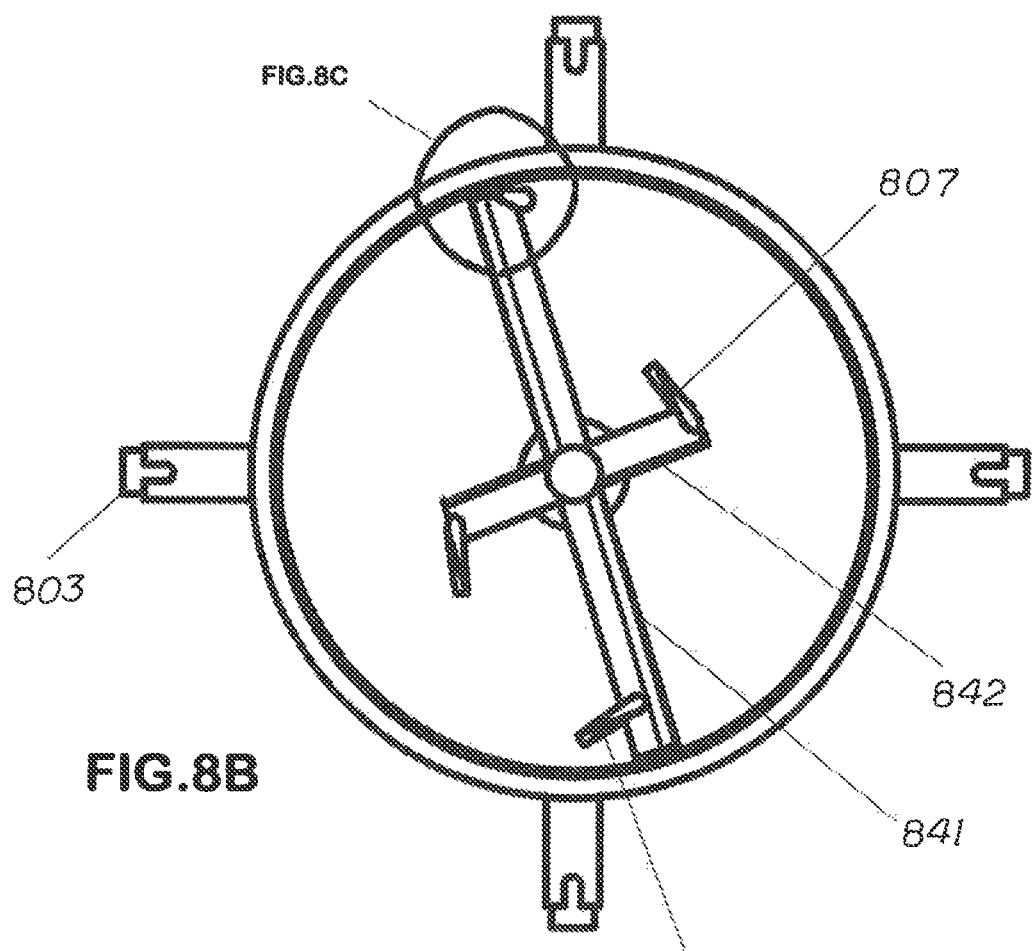
FIG. 8B depicts a top-down perspective view of the vertical cylindrical reactor vessel. This exemplary embodiment shows two sets of support bars that may rotate in opposite directions.

FIG. 8B is a top-down perspective view of the of the vertical cylindrical reactor vessel 80 along the line A-A of FIG. 8A. A vessel support stand 803 supports the vertical cylindrical reactor vessel 80. In this exemplary embodiment, there are two sets of support bars that support two sets of paddles 83 moving in opposite directions. The scrapper support bar 841 supports a scrapper paddle 805 on one end and an opposing paddle 806 on the opposite end. In this example embodiment, the scrapper paddle support bar moves in a counter-clockwise direction. The opposing paddle 806 does not contact the inner wall of the mixing chamber 820 (as shown in FIG. 8C), rather it directs a portion of the biomass and enzyme material in the mixing chamber towards the inner wall of the mixing chamber 820 (as shown in FIG. 8C).

The paddle support bar 842 may support one or more paddles 807. In this example embodiment, the paddle support bar rotates in a clockwise direction.

Figure 8C:
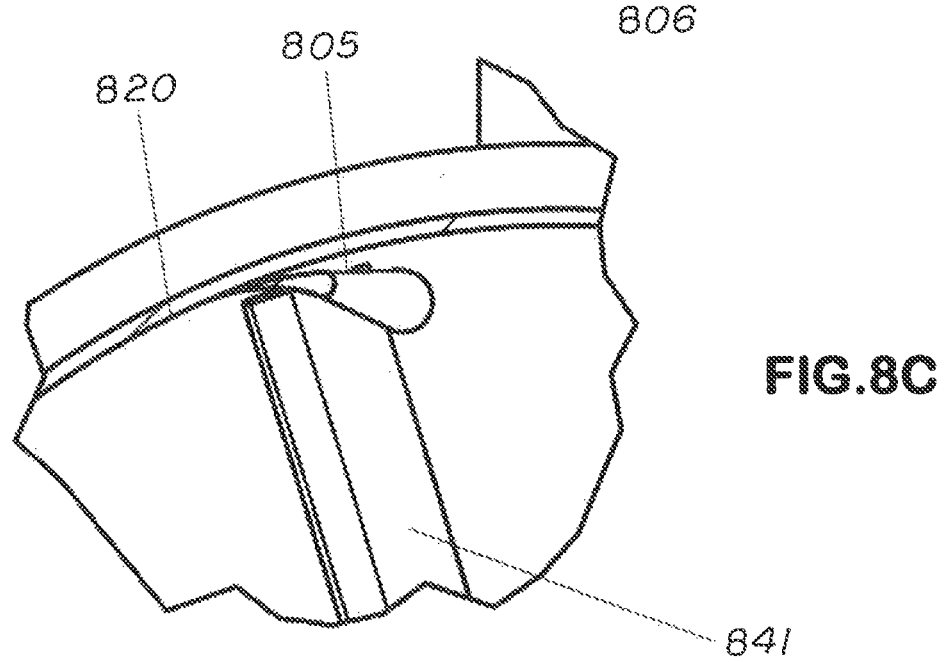
FIG. 8C is a close-up of the outer support bar of FIG. 8B. This support bar has a scrapper baffle that may dislodge accumulations of biomass and enzyme material from the inner wall of the mixing chamber.

FIG. 8C is a detailed area of FIG. 8B showing the scrapper paddle 805 engaging the inner wall of the mixing chamber 820. The scrapper may dislodge accumulations of biomass and enzyme material on the inner wall of the mixing chamber 820. The scrapper paddle 805 may be a modified paddle configured according to any previously listed paddle embodiments. For example, the angle of attack and the cross sectional area of the scrapper paddle 805 may vary along the vertical length of the scrapper paddle 805.

The invention has been described in detail for purposes of clarity and understanding. However, it will be appreciated that certain changes and modifications to the disclosed embodiments of the invention may be practiced within the scope of the claims of the invention.

What is claimed is:

1. A reactor vessel assembly for the continuous enzymatic conversion of biomass to monomeric sugars, the reactor vessel assembly comprising:
   a source of biomass;
   a source of at least one enzyme;
   a mixing chamber having a vertical length greater than a horizontal width of the mixing chamber, an upper inlet connected to receive biomass from the source of biomass and to receive at least one enzyme from the source of the at least one enzyme, and a lower outlet, wherein the lower outlet is open to discharge a mixture from the mixing chamber while the upper inlet is open to receive the biomass and the at least one enzyme; and
   at least one paddle having a length oriented vertically within the mixing chamber and a width oriented horizontally and smaller than the length, wherein the at least one paddle extends at least fifty percent of the vertical length of the mixing chamber and the at least one paddle having a cross-sectional shape in a horizontal direction of one of a teardrop, diamond, crescent, ellipse and airfoil, wherein the at least one paddle moves in a circular path about a vertical axis of the chamber while maintaining the vertical orientation, and
   the at least one paddle forms an angle of attack with respect to a tangent to the circular path of the paddle and the angle of attack is no greater than twenty five degrees.

2. The reactor vessel assembly of claim 1, wherein the at least one paddle extends substantially the entire of the vertical length of the mixing chamber.

3. The reactor vessel assembly of claim 1, wherein the vertical length of the mixing chamber is at least one hundred feet and a diameter of the mixing chamber is at least 30 feet.

4. The reactor vessel assembly of claim 1 further comprising a center shaft coupled to the at least one paddle.

5. The reactor vessel assembly of claim 1, wherein the at least one paddle is in an array of paddles arranged symmetrically about a vertical axis of the mixing chamber.

6. The reactor vessel assembly of claim 1 further comprising an upper support bar and a lower support bar coupled, respectively, to opposite end regions of the at least one paddle.

7. The reactor vessel assembly of claim 6 further comprising a center shaft coaxial with a center axis of the mixing chamber, and the upper support bar is connected to an upper section of the center shaft and the lower support bar is connected to a lower section of the center shaft.

8. The reactor vessel assembly of claim 1, wherein the at least one paddle has a non-uniform cross-sectional shape along the length of the paddle.

9. The reactor vessel assembly of claim 1, wherein the angle of attack of the at least one paddle is non-uniform along the length of the at least one paddle.

10. The reactor vessel assembly of claim 9, wherein the offset angle from the vertical axis is in a range between negative 15 degrees and positive 15 degrees.

11. A reactor vessel assembly for continuous enzymatic conversion of biomass to monomeric sugars by mixing biomass with enzymes to promote hydrolysis comprising:
    a source of biomass;
    a source of at least one enzyme;
    an internal cylindrical mixing chamber having a vertical length greater than a horizontal width of the mixing chamber, an upper inlet connected to receive biomass from the source of biomass and to receive at least one enzyme from the source of the at least one enzyme, and a lower outlet, wherein the lower outlet is open to discharge a mixture from the chamber while the upper inlet is open to receive the biomass and the at least one enzyme;

a vertical center shaft extending the length of the internal cylindrical mixing chamber, a motor drivingly coupled to the center shaft, an upper support bar within the internal cylindrical mixing chamber and extending outward from an upper section of the center shaft, a lower support bar within the internal cylindrical mixing chamber and extending outward from a lower section of the center shaft; and at least one vertical paddle supported by and attached to the upper support bar and the lower support bar, wherein the at least one vertical paddle moves around the center shaft, wherein the at least one vertical paddle extends at least fifty percent of the vertical length of the mixing chamber and the at least one vertical paddle has a horizontal cross section having a shape of at least one of a teardrop, diamond, crescent, ellipse and airfoil, and a width of the at least one vertical paddle is and smaller than the length of the paddle, and wherein the at least one paddle forms an angle of attack with respect to a tangent to a circular path of the paddle about the center shaft and the angle of attack is no greater than twenty five degrees.

12. The reactor vessel assembly of claim 11, wherein a vertical paddle movement promotes a horizontal movement of a slurry of biomass and enzyme material in the internal cylindrical mixing chamber.

13. The reactor vessel assembly of claim 11 further comprising a scrapper baffle supported by a scrapper support bar extending radially from the center shaft wherein the scrapper baffle engages an inner wall of the mixing chamber.

14. The reactor vessel assembly of claim 11, wherein the angle of attach of the at least one vertical paddle is non-uniform along the length of the at least one vertical paddle.

15. The reactor vessel assembly of claim 14, wherein the offset angle from the vertical axis is in a range between negative 15 degrees and positive 15 degrees.

16. A reactor vessel, assembly for continuous enzymatic conversion of biomass to monomeric sugars by mixing of biomass with an enzyme to promote hydrolysis, wherein the reactor vessel comprises:

a source of biomass;

a source of at least one enzyme;

an internal cylindrical mixing chamber, having a vertical length greater than a horizontal width of the mixing chamber, an upper inlet connected to receive biomass from the source of biomass and to receive at least one enzyme from the source of the at least one enzyme, and a lower outlet, wherein the lower outlet is open to discharge a mixture from the chamber while the upper inlet is open to receive the biomass and the at least one enzyme;

a vertical center shaft coaxial to a vertical axis of the internal cylindrical mixing chamber, extending into the chamber from below the chamber;

a motor drivingly coupled to the center shaft;

an upper support bar within the internal cylindrical mixing chamber and extending outward from an upper section of the center shaft;

a lower support bar within the internal cylindrical mixing chamber and extending outward from a lower section of the center shaft; and at least one vertical paddle supported by and attached to the upper support bar and the lower support bar, wherein the at least one vertical paddle moves in a circular path around the center shaft, wherein the at least one vertical paddle extends at least fifty percent of the vertical length of the mixing chamber and the at least one vertical paddle has a horizontal cross section having a shape of at least one of a teardrop, diamond, crescent, ellipse and airfoil, and a width of the at least one vertical paddle is and smaller than the length of the paddle, wherein the at least one paddle forms an angle of attack with respect to a tangent to the circular path and the angle of attack is no greater than twenty five degrees, and wherein the center shaft extends vertically into the mixing chamber no more than the upper support bar.

17. A reactor vessel assembly for the continuous enzymatic conversion of biomass to monomeric sugars particularly the mixing of biomass with enzymes to promote hydrolysis comprising:

a source of biomass;

a source of at least one enzyme;

a cylindrical mixing chamber having a vertical axis and a vertical length greater than a horizontal width of the mixing chamber, an upper inlet connected to continuously receive biomass from the source of biomass and to receive at least one enzyme from the source of the at least one enzyme, and a lower outlet connected to continuously discharge a mixture from the chamber while the upper inlet receives the biomass and the at least one enzyme;

at least one vertical paddle supported by an upper support bar and a lower support bar, wherein the at least one vertical paddle extends at least fifty percent of the vertical length of the mixing chamber;

a center shaft extending along the vertical axis of the cylindrical mixing chamber, wherein the upper and lower support bars are attached to and extend radially outward from the center shaft, wherein the at least one vertical paddle forms an angle of attack with respect to a circular path of the paddle about the vertical axis and the angle of attack is no greater than twenty five degrees;

an engine or motor external to the reactor vessel and drivingly coupled to the center shaft to rotate the center shaft, an upper support bar and a lower support bar and the at least one vertical paddle; and a conical deflector having a peak aligned with the vertical axis and positioned above the at least one vertical paddle.

18. The reactor vessel assembly of claim 17, wherein the conical deflector has a lower edge having a perimeter which is at various radial lengths from the vertical axis.

19. The reactor vessel assembly of claim 17, wherein the lower edge is stepped, such that the lower edge is at various radial distances from the vertical axis.

20. The reactor vessel assembly of claim 17, wherein the conical deflector has cutouts and an irregular lower edge to distribute a biomass and enzyme material into the cylindrical mixing chamber.

21. The reactor vessel assembly of claim 17, wherein the conical deflector distributes a biomass and enzyme slurry material across the cylindrical mixing chamber.

22. The reactor vessel assembly of claim 17 further comprising a scrapper baffle supported by a scrapper support bar extending radially from the center shaft wherein the scrapper baffle engages an inner wall of the mixing chamber.

* * * * *